(12) United States Patent
Siegal et al.

(10) Patent No.: US 9,408,712 B2
(45) Date of Patent: Aug. 9, 2016

(54) SURGICAL SYSTEMS AND METHODS FOR IMPLANTING DEFLECTABLE IMPLANTS

(71) Applicant: NLT SPINE LTD, Kfar Saba (IL)

(72) Inventors: Tzony Siegal, Moshav Shoeva (IL); Oded Loebl, Tel Mond (IL); Didier Toubia, Raanana (IL)

(73) Assignee: NLT-SPINE LTD., Kfar Saba (IL)

( * ) Notice: Subject to any disclaimer, the term of this patent is extended or adjusted under 35 U.S.C. 154(b) by 0 days.

(21) Appl. No.: 14/608,231

(22) Filed: Jan. 29, 2015

(65) Prior Publication Data

US 2015/0142118 A1    May 21, 2015

Related U.S. Application Data

(63) Continuation of application No. 13/810,225, filed as application No. PCT/IB2011/053143 on Jul. 14, 2011, now Pat. No. 8,986,388.

(60) Provisional application No. 61/364,412, filed on Jul. 15, 2010.

(51) Int. Cl.
*A61F 2/44* (2006.01)
*A61B 17/88* (2006.01)
(Continued)

(52) U.S. Cl.
CPC .............. *A61F 2/442* (2013.01); *A61F 2/4455* (2013.01); *A61F 2/4465* (2013.01);
(Continued)

(58) Field of Classification Search
CPC ........ A61F 2/4455–2/447; A61F 2002/30471; A61F 2002/30187
See application file for complete search history.

(56) References Cited

U.S. PATENT DOCUMENTS 4,759,769 A    7/1988  Hedman et al.
5,059,193 A   10/1991  Kuslich
(Continued)

FOREIGN PATENT DOCUMENTS

DE    2263842    7/1974
DE    9107494    9/1991
(Continued)

OTHER PUBLICATIONS

E. AliCl, et al "Prostheses Designed for Vertebral Body Replacement" in Journal of Biomechanics vol. 23 1990, No. 8, pp. 799-809.
(Continued)

*Primary Examiner* — Jacqueline Johanas
(74) *Attorney, Agent, or Firm* — Mark M. Friedman

(57) ABSTRACT

Deflectable implants, systems and methods for implanting deflectable implants are disclosed. The deflectable implant includes at least one sequence of segments, the sequence includes at least two segments, the segments being interconnected at effective hinges, the sequence assuming a straightened or low curvature insertion state for insertion into the body, the sequence being deflectable to a fully deflected state defined by abutment of abutment features of adjacent of the segments. The deflectable implant includes further a linkage mechanically linked to at least part of at least one of the sequences of segments for deflecting the at least one sequence of segments from the insertion state towards the fully deflected state wherein the at least one sequence is at least part of a loop structure assuming a low profile folded state with the at least one sequence in the insertion state, and wherein deflection of the at least one sequence towards the fully deflected state generates an open state of the loop structure and wherein the loop defines an enclosed volume.

14 Claims, 23 Drawing Sheets

(51) Int. Cl.
 *A61F 2/30* (2006.01)
 *A61F 2/46* (2006.01)
 *A61F 2/28* (2006.01)

(52) U.S. Cl.
 CPC .......... *A61F 2/4611* (2013.01); *A61F 2/30965* (2013.01); *A61F 2/44* (2013.01); *A61F 2/4601* (2013.01); *A61F 2002/2817* (2013.01); *A61F 2002/2835* (2013.01); *A61F 2002/302* (2013.01); *A61F 2002/305* (2013.01); *A61F 2002/30126* (2013.01); *A61F 2002/30179* (2013.01); *A61F 2002/30471* (2013.01); *A61F 2002/30579* (2013.01); *A61F 2002/4415* (2013.01); *A61F 2002/4475* (2013.01); *A61F 2002/4635* (2013.01); *A61F 2210/0019* (2013.01); *A61F 2220/0025* (2013.01); *A61F 2220/0091* (2013.01); *A61F 2230/0008* (2013.01); *A61F 2230/0065* (2013.01); *A61F 2250/0058* (2013.01); *A61F 2310/00017* (2013.01); *A61F 2310/00023* (2013.01)

(56) References Cited

U.S. PATENT DOCUMENTS

| | | | |
|---|---|---|---|
| 5,171,278 A | 12/1992 | Pisharodi | |
| 5,258,031 A | 11/1993 | Salib et al. | |
| 5,390,683 A | 2/1995 | Pisharodi | |
| 5,534,029 A | 7/1996 | Shima | |
| 5,599,279 A | 2/1997 | Slotman | |
| 5,620,458 A | 4/1997 | Green et al. | |
| 6,039,761 A | 3/2000 | Li et al. | |
| 6,080,193 A | 6/2000 | Hochshuler et al. | |
| 6,126,689 A | 10/2000 | Brett | |
| 6,190,414 B1 | 2/2001 | Young et al. | |
| 6,238,403 B1 | 5/2001 | Greene, Jr. et al. | |
| 6,332,894 B1 | 12/2001 | Stalcup et al. | |
| 6,375,682 B1 | 4/2002 | Fleischmann et al. | |
| 6,387,130 B1 | 5/2002 | Stone et al. | |
| 6,419,705 B1 | 7/2002 | Erikson | |
| 6,443,989 B1 | 9/2002 | Jackson | |
| 6,491,724 B1 | 12/2002 | Ferree | |
| 6,576,016 B1 | 6/2003 | Hochshuler et al. | |
| 6,582,451 B1 | 6/2003 | Marucci et al. | |
| 6,620,196 B1 | 9/2003 | Trieu | |
| 6,641,614 B1 | 11/2003 | Wagner et al. | |
| 6,676,665 B2* | 1/2004 | Foley | A61B 17/025 600/201 |
| 6,706,070 B1 | 3/2004 | Wagner et al. | |
| 6,830,589 B2 | 12/2004 | Erikson | |
| 7,070,598 B2 | 7/2006 | Lim et al. | |
| 7,087,055 B2 | 8/2006 | Lim et al. | |
| 7,097,648 B1 | 8/2006 | Globerman et al. | |
| 7,431,735 B2 | 10/2008 | Liu et al. | |
| 7,625,377 B2 | 12/2009 | Veldhuizen et al. | |
| 7,655,046 B2 | 2/2010 | Dryer et al. | |
| 7,720,282 B2 | 5/2010 | Blake et al. | |
| 7,763,028 B2 | 7/2010 | Lim et al. | |
| 7,799,081 B2 | 9/2010 | McKinley | |
| 7,846,206 B2 | 12/2010 | Oglaza et al. | |
| 7,901,409 B2* | 3/2011 | Canaveral | A61B 17/8858 600/222 |
| 7,905,920 B2 | 3/2011 | Galea | |
| 7,909,872 B2 | 3/2011 | Zipnick et al. | |
| 7,938,860 B2 | 5/2011 | Trieu | |
| 7,947,078 B2 | 5/2011 | Siegal | |
| 7,959,652 B2 | 6/2011 | Zucherman et al. | |
| 8,021,429 B2 | 9/2011 | Viker | |
| 8,025,665 B2 | 9/2011 | Lim et al. | |
| 8,062,375 B2 | 11/2011 | Glerum et al. | |
| 8,123,809 B2 | 2/2012 | Melkent et al. | |
| 8,133,232 B2 | 3/2012 | Levy et al. | |
| 8,187,332 B2 | 5/2012 | Mcluen et al. | |
| 8,292,963 B2 | 10/2012 | Miller et al. | |
| 8,303,658 B2 | 11/2012 | Peterman | |
| 8,308,802 B2 | 11/2012 | Rhoda et al. | |
| 8,317,798 B2 | 11/2012 | Lim et al. | |
| 8,317,802 B1 | 11/2012 | Manzi et al. | |
| 8,317,866 B2 | 11/2012 | Palmatier et al. | |
| 8,323,344 B2 | 12/2012 | Galley et al. | |
| 8,337,531 B2 | 12/2012 | Johnson et al. | |
| 8,337,559 B2 | 12/2012 | Hansell et al. | |
| 8,343,193 B2 | 1/2013 | Johnson et al. | |
| 8,349,013 B2 | 1/2013 | Zucherman et al. | |
| 8,349,014 B2 | 1/2013 | Barreiro et al. | |
| 8,377,071 B2 | 2/2013 | Lim et al. | |
| 8,398,713 B2 | 3/2013 | Weiman | |
| 8,403,990 B2 | 3/2013 | Dryer et al. | |
| 8,444,697 B1 | 5/2013 | Butler et al. | |
| 8,518,120 B2 | 8/2013 | Glerum et al. | |
| 8,523,944 B2 | 9/2013 | Jimenez et al. | |
| 8,556,979 B2 | 10/2013 | Glerum et al. | |
| 8,579,907 B2 | 11/2013 | Lim et al. | |
| 8,628,576 B2 | 1/2014 | Triplett et al. | |
| 8,628,577 B1 | 1/2014 | Jimenez | |
| 8,679,183 B2 | 3/2014 | Glerum et al. | |
| 8,685,098 B2 | 4/2014 | Glerum et al. | |
| 8,709,086 B2 | 4/2014 | Glerum | |
| 8,771,360 B2 | 7/2014 | Jimenez et al. | |
| 8,870,959 B2 | 10/2014 | Arnin | |
| 9,017,413 B2* | 4/2015 | Siegal | A61F 2/442 606/105 |
| 2002/0015197 A1 | 2/2002 | Nakashima | |
| 2003/0236520 A1 | 12/2003 | Lim et al. | |
| 2004/0059418 A1 | 3/2004 | McKay et al. | |
| 2004/0133280 A1 | 7/2004 | Trieu | |
| 2004/0162618 A1 | 8/2004 | Mujwid et al. | |
| 2004/0193158 A1 | 9/2004 | Lim et al. | |
| 2005/0113920 A1 | 5/2005 | Foley et al. | |
| 2005/0125062 A1 | 6/2005 | Biedermann | |
| 2005/0143827 A1 | 6/2005 | Globerman et al. | |
| 2005/0182416 A1* | 8/2005 | Lim | A61B 17/025 606/90 |
| 2005/0209698 A1 | 9/2005 | Gordon | |
| 2005/0228391 A1 | 10/2005 | Levy | |
| 2005/0261683 A1* | 11/2005 | Veldhuizen | A61F 2/44 623/17.11 |
| 2005/0278036 A1 | 12/2005 | Leonard et al. | |
| 2006/0004455 A1 | 1/2006 | Leonard et al. | |
| 2006/0041258 A1 | 2/2006 | Galea | |
| 2006/0085070 A1* | 4/2006 | Kim | A61F 17/7065 623/17.11 |
| 2006/0142858 A1 | 6/2006 | Colleran et al. | |
| 2006/0224241 A1 | 10/2006 | Butler et al. | |
| 2006/0235423 A1 | 10/2006 | Cantu | |
| 2006/0247778 A1 | 11/2006 | Ferree et al. | |
| 2007/0032791 A1 | 2/2007 | Greenhalgh | |
| 2007/0073398 A1 | 3/2007 | Fabian et al. | |
| 2007/0123986 A1 | 5/2007 | Schaller | |
| 2007/0173939 A1 | 7/2007 | Kim et al. | |
| 2007/0233245 A1 | 10/2007 | Trieu et al. | |
| 2007/0282449 A1* | 12/2007 | de Villiers | A61F 2/4425 623/17.15 |
| 2008/0119853 A1 | 5/2008 | Felt et al. | |
| 2008/0125865 A1 | 5/2008 | Abdelgany | |
| 2008/0243255 A1 | 10/2008 | Butler | |
| 2008/0312743 A1 | 12/2008 | Vila et al. | |
| 2009/0216274 A1 | 8/2009 | Morancy-Meister et al. | |
| 2009/0270873 A1 | 10/2009 | Fabian | |
| 2010/0131009 A1 | 5/2010 | Roebling et al. | |
| 2010/0286771 A1 | 11/2010 | Villiers et al. | |
| 2011/0276141 A1* | 11/2011 | Caratsch | A61F 2/4455 623/17.16 |
| 2012/0004732 A1* | 1/2012 | Goel | A61F 2/4455 623/17.16 |
| 2012/0029639 A1 | 2/2012 | Blackwell et al. | |
| 2012/0083889 A1 | 4/2012 | Purcell et al. | |
| 2012/0123546 A1 | 5/2012 | Medina | |
| 2012/0215316 A1 | 8/2012 | Mohr | |
| 2013/0018466 A1 | 1/2013 | Yu et al. | |
| 2013/0041471 A1 | 2/2013 | Siegal | |
| 2013/0066374 A1 | 3/2013 | Galley et al. | |
| 2013/0158664 A1 | 6/2013 | Palmatier | |

(56) References Cited

U.S. PATENT DOCUMENTS

| | | |
|---|---|---|
| 2013/0158669 A1 | 6/2013 | Sangarian et al. |
| 2013/0190876 A1 | 7/2013 | Drochner et al. |
| 2013/0317615 A1 | 11/2013 | Jimenez et al. |
| 2013/0325128 A1 | 12/2013 | Perloff |
| 2014/0005787 A1 | 1/2014 | Dmuschewsky |
| 2014/0052254 A1 | 2/2014 | Glerum et al. |
| 2014/0114429 A1 | 4/2014 | Slone et al. |
| 2014/0156007 A1 | 6/2014 | Pabst et al. |
| 2014/0243982 A1 | 8/2014 | Miller |
| 2014/0249629 A1 | 9/2014 | Moskowitz |

FOREIGN PATENT DOCUMENTS

| | | |
|---|---|---|
| DE | 4416605 | 6/1995 |
| FR | 2717068 | 9/1995 |
| WO | 98/34552 | 8/1998 |
| WO | 03003951 | 1/2003 |
| WO | PCT/GB2007/003927 | 10/2007 |
| WO | 2008084479 | 7/2008 |
| WO | 2012117312 | 9/2012 |
| WO | PCT/US2012/067227 | 11/2012 |
| WO | 2013052807 | 4/2013 |
| WO | 2014091029 | 6/2014 |

OTHER PUBLICATIONS

E. AliCl et al "Prostheses Designed for Vertebral Body Replacement" in Journal of Biomechanics vol. 23 1990 No. 8, pp. 799-809.

* cited by examiner

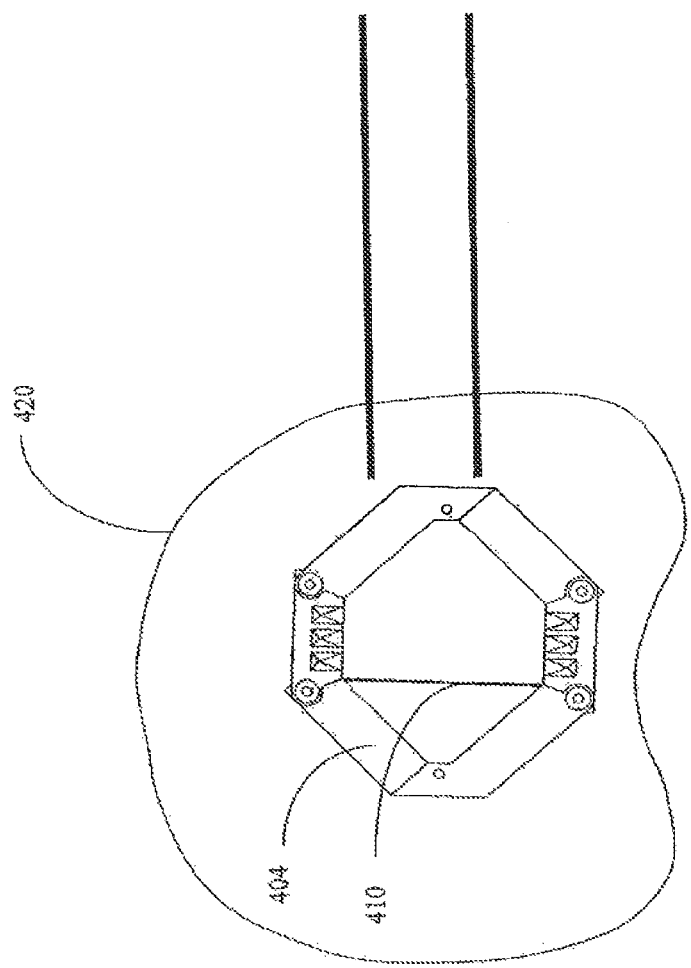

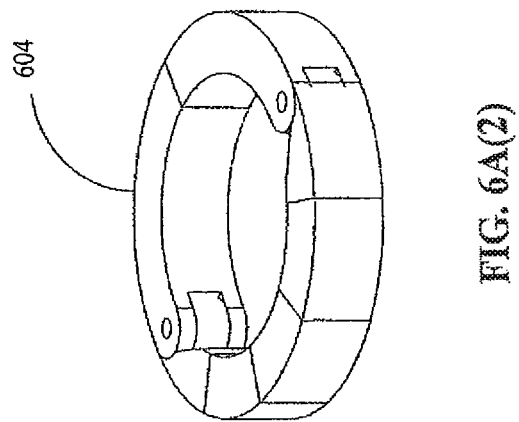
FIG. 6A(2)
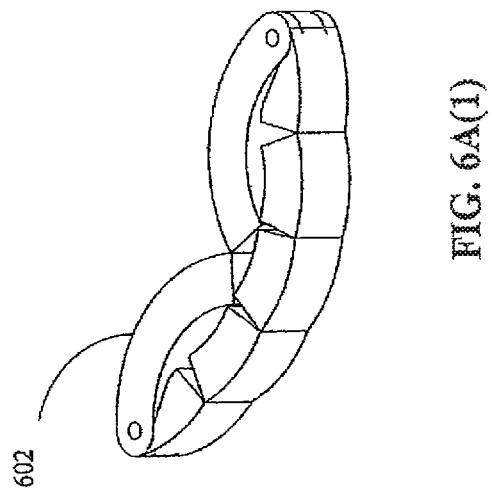
FIG. 6A(1)

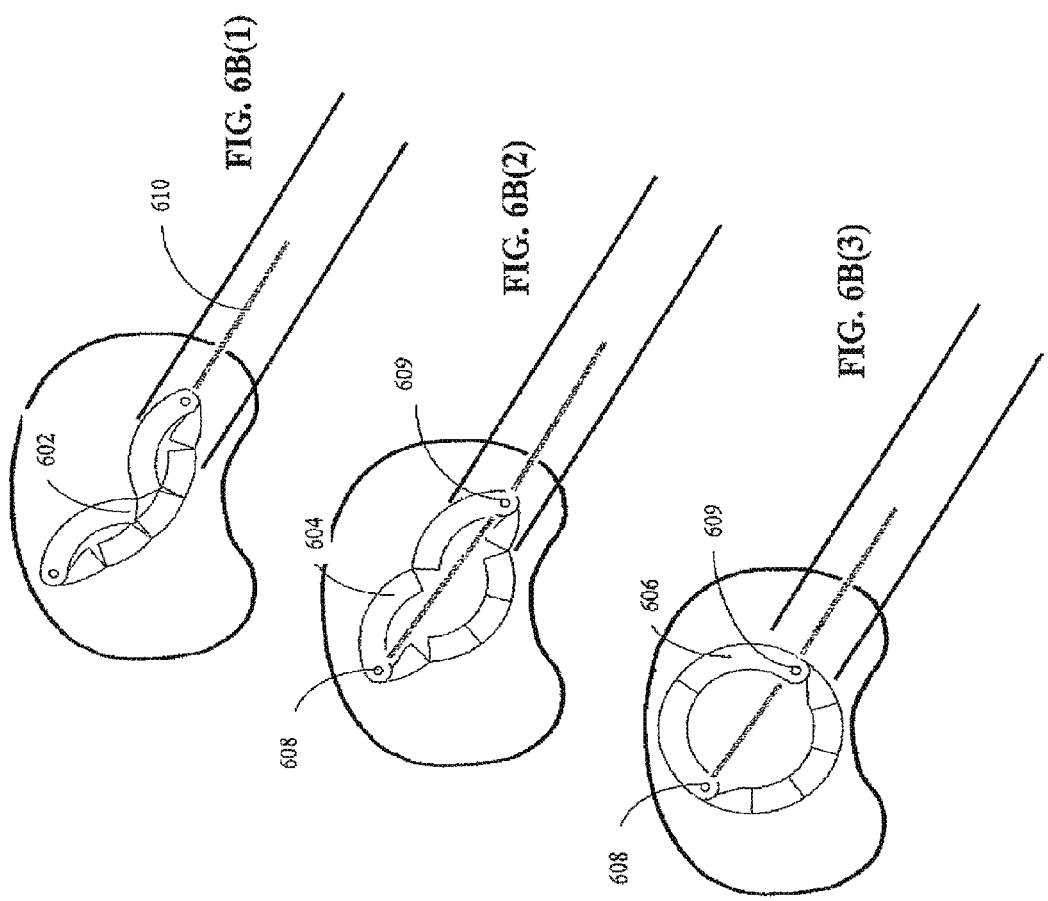

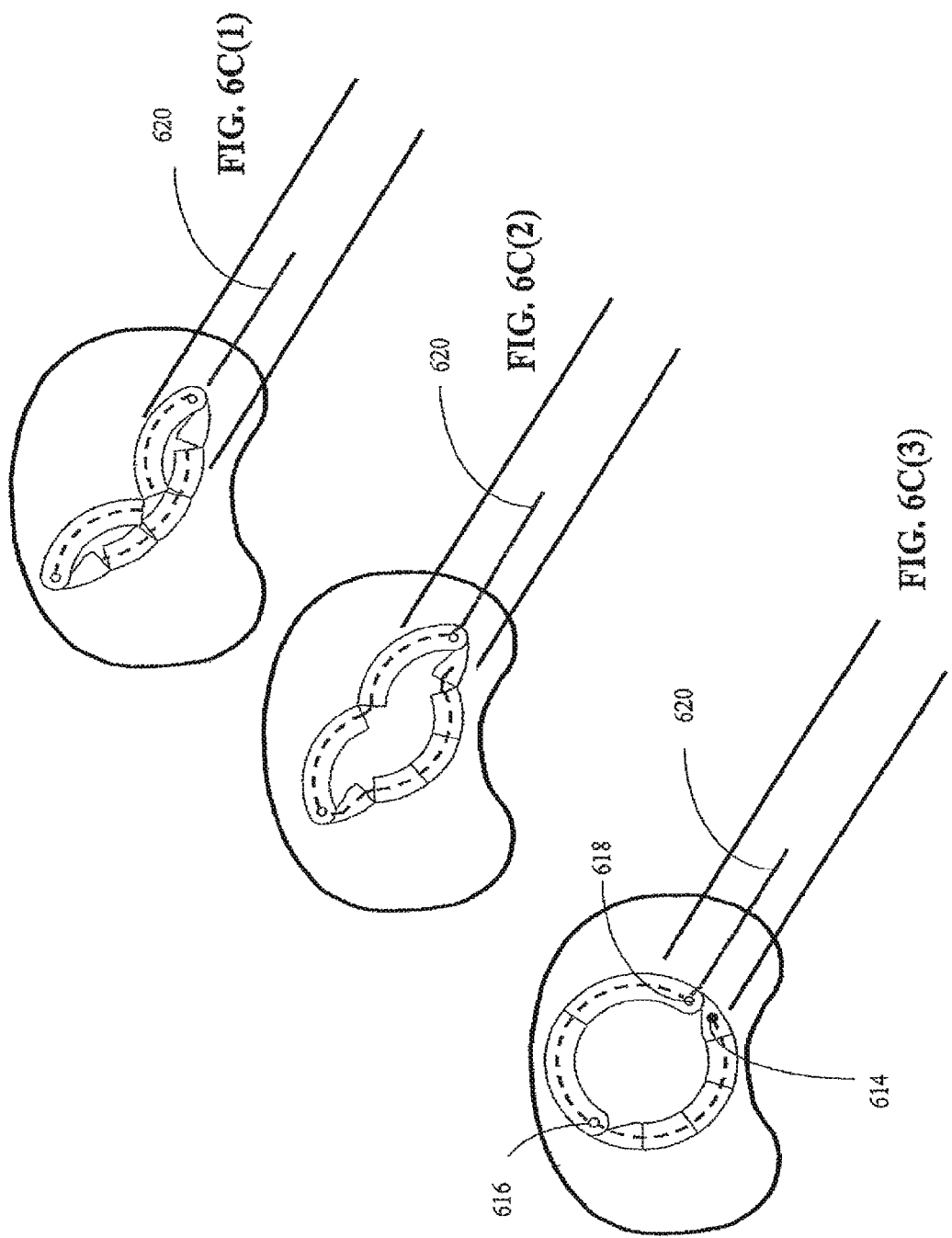

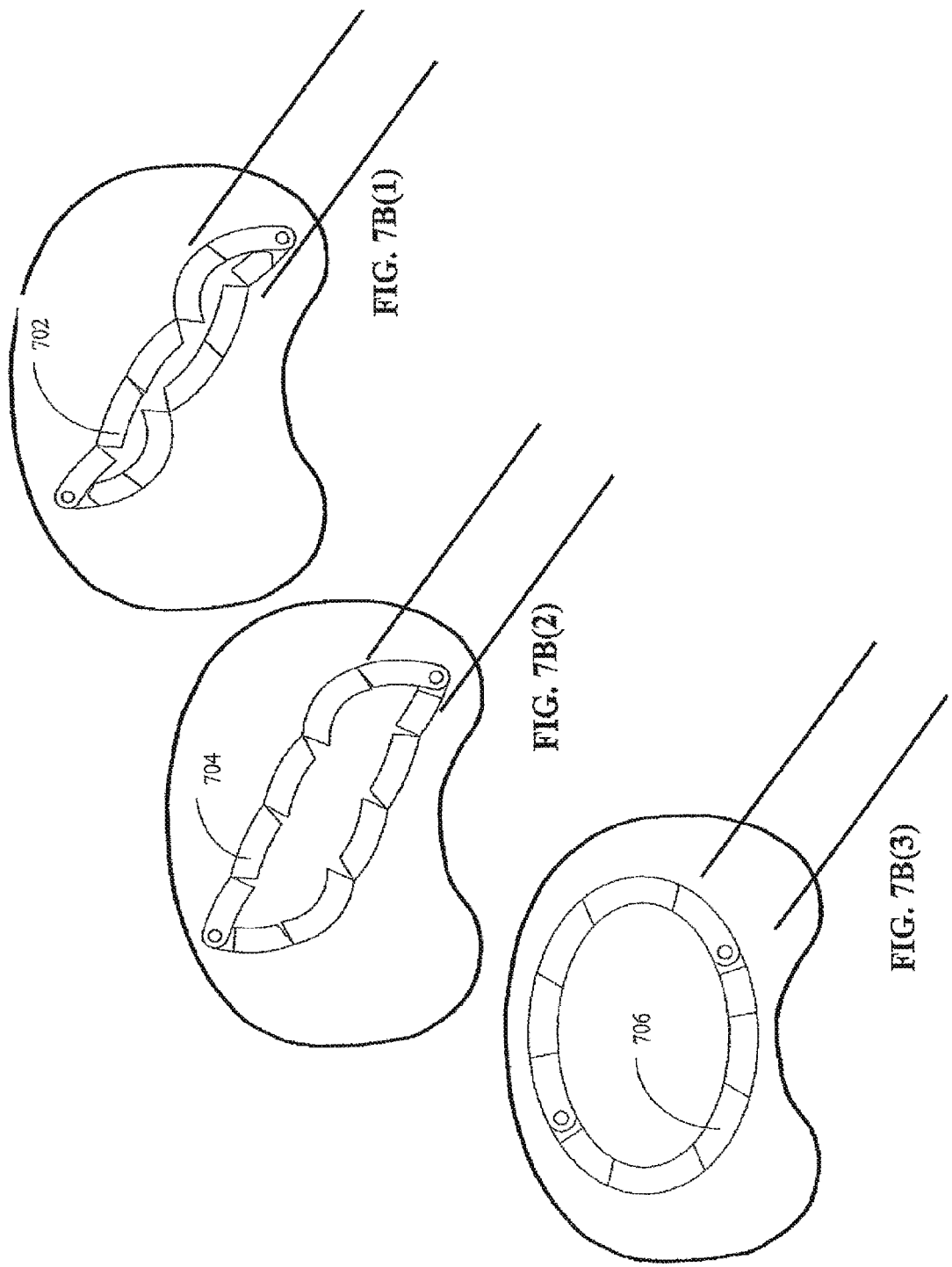

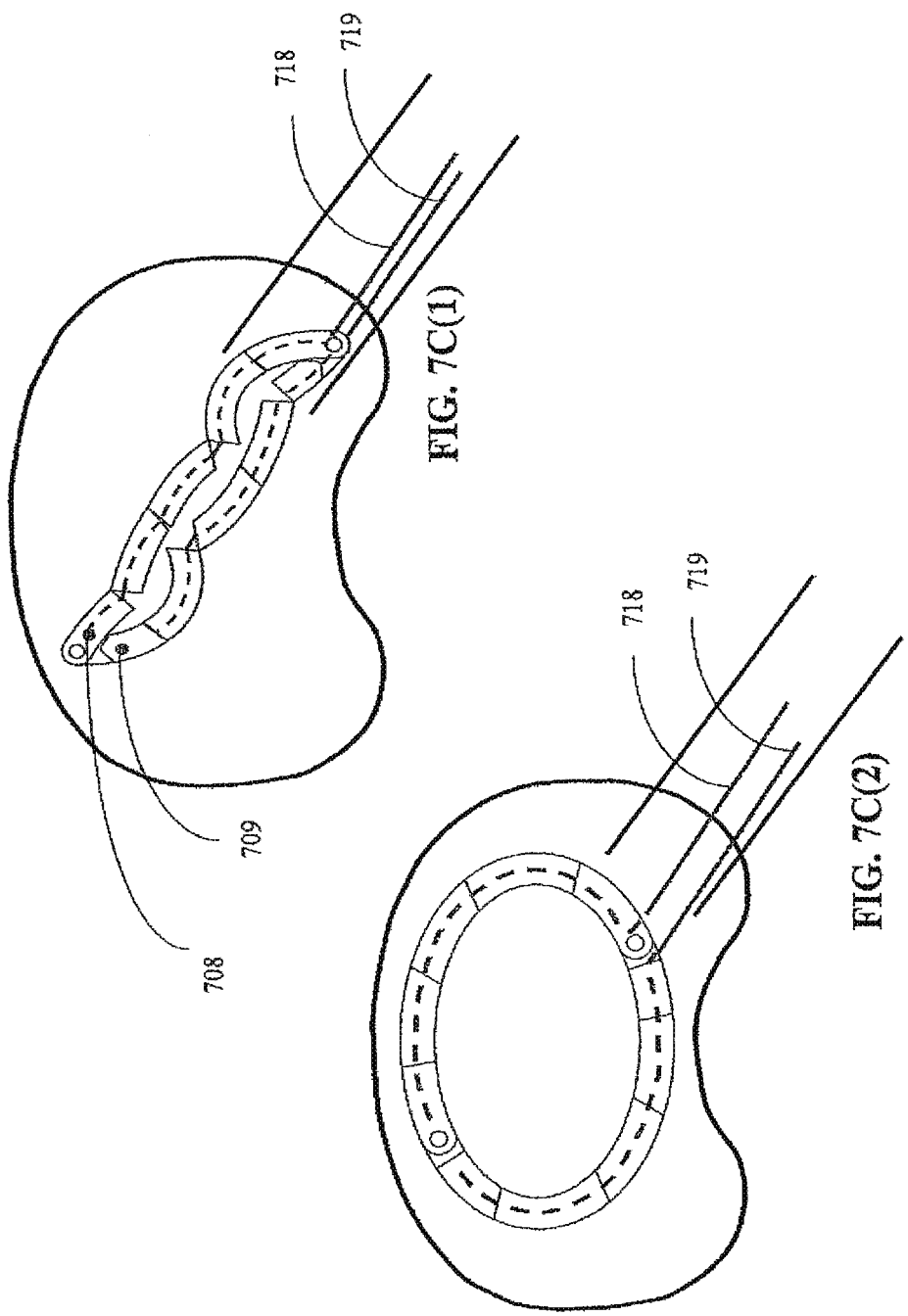

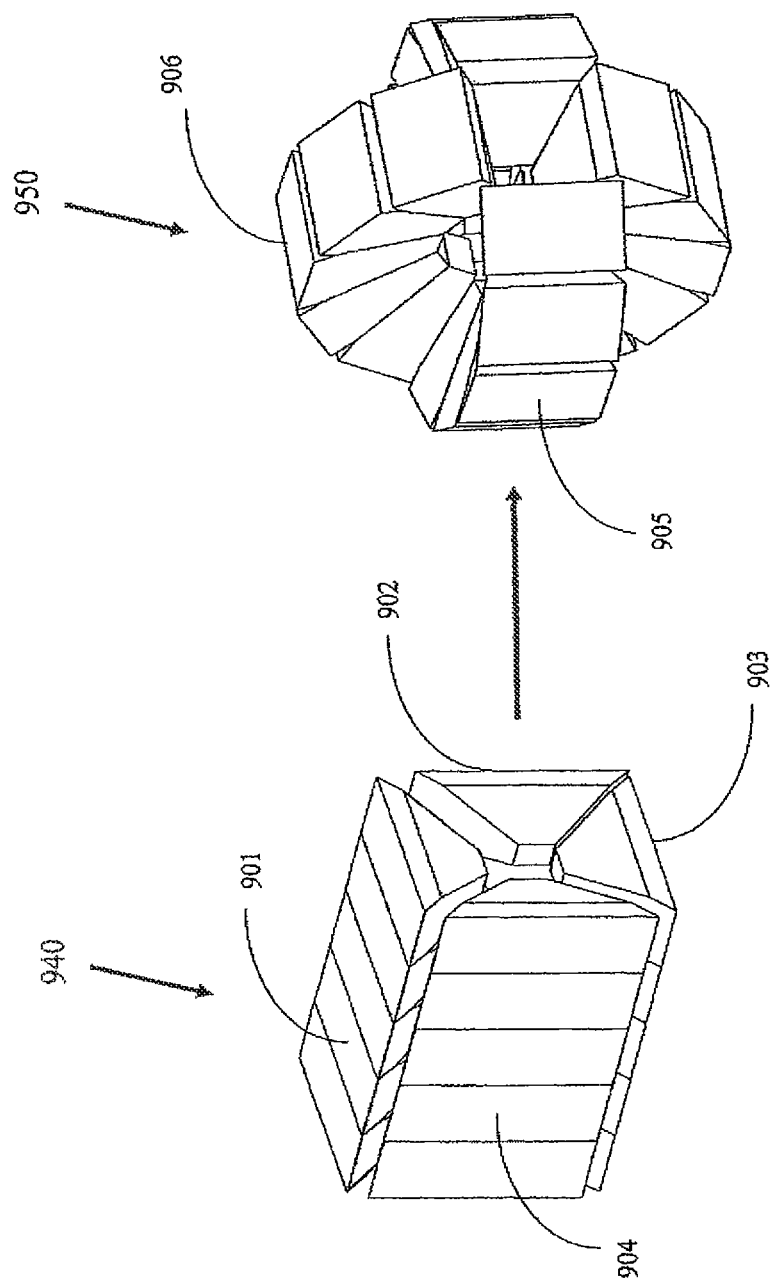

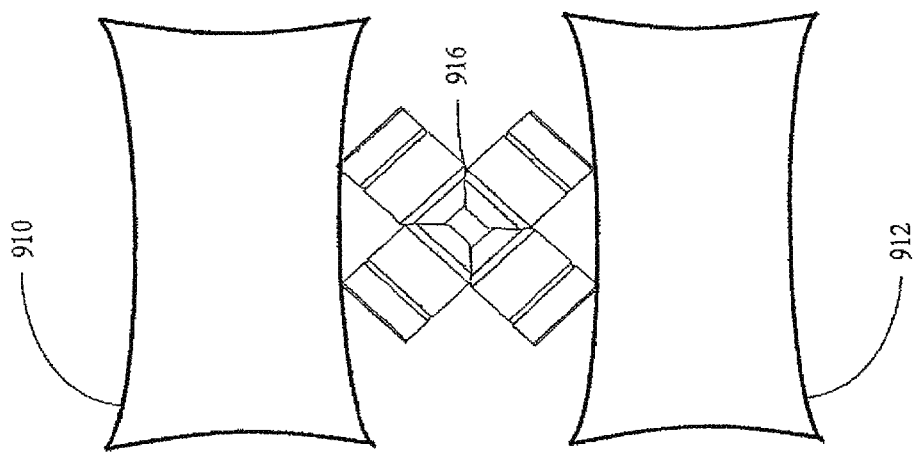
FIG. 9B(2)
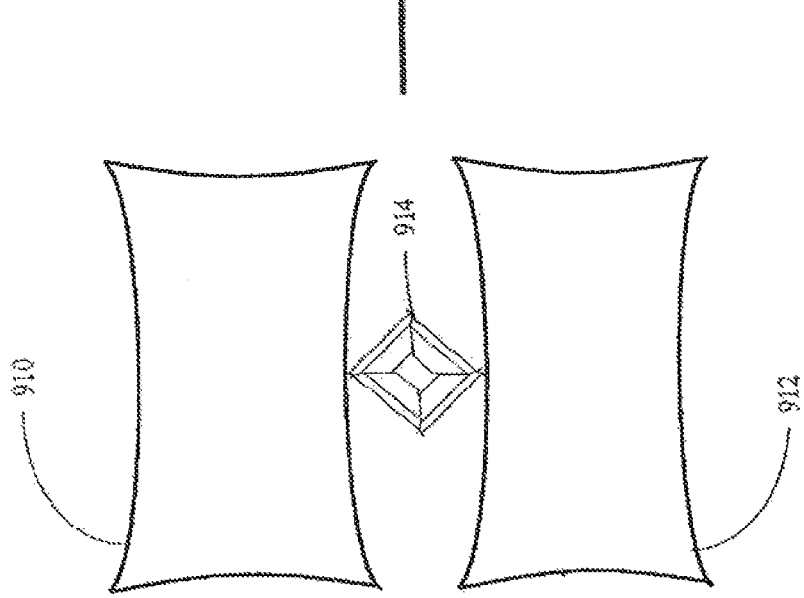
FIG. 9B(1)

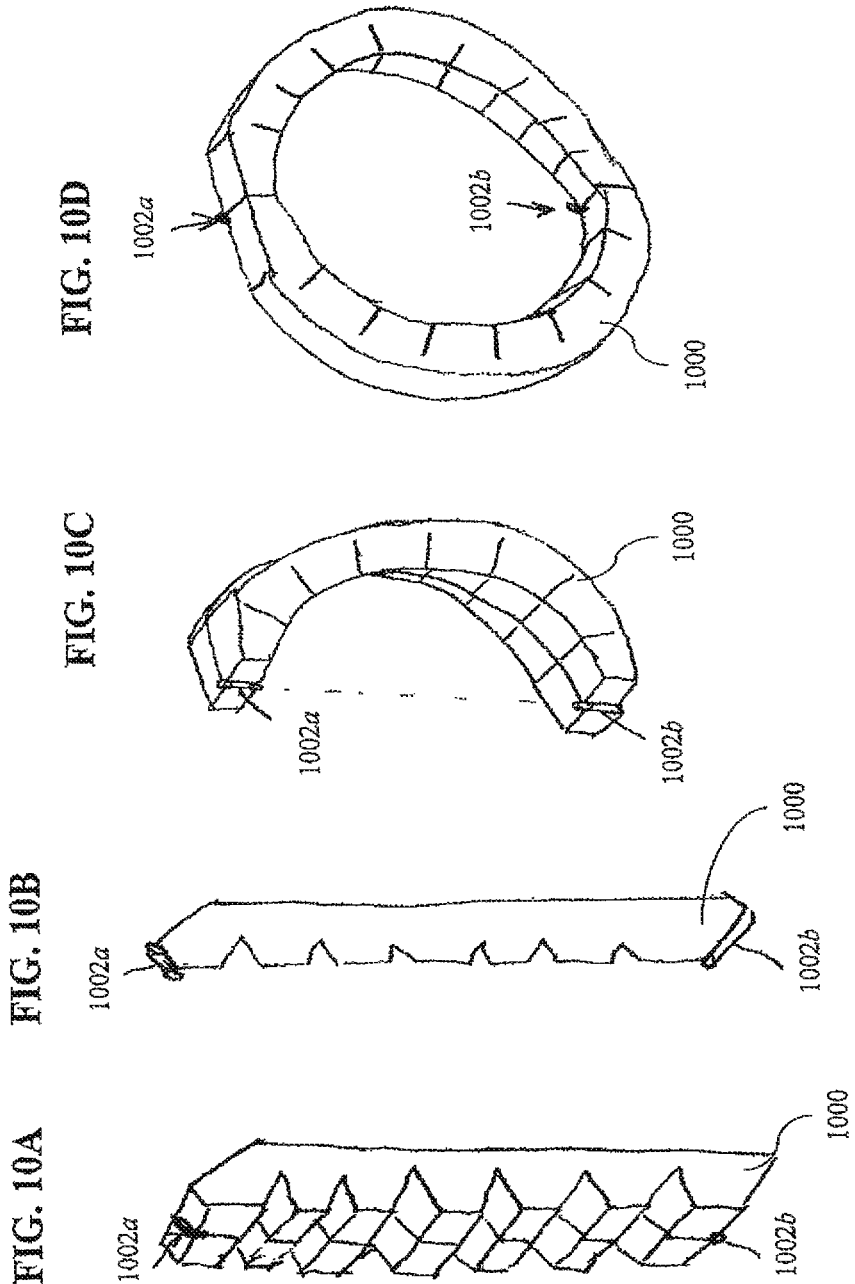

SURGICAL SYSTEMS AND METHODS FOR IMPLANTING DEFLECTABLE IMPLANTS

FIELD OF THE INVENTION

The invention relates generally to implants, and more particularly to systems and methods for implanting deflectable implants.

BACKGROUND OF THE INVENTION

Minimally invasive subcutaneous procedures, which are performed through a small orifice in the skin, limit the size of the surgery tools and implants that are used.

Hence it would be highly advantageous to develop implants that have small cross sections such that they can be inserted easily through a small orifice in the skin and be deflected into their final functional expanded shape at the intended implantation site in the body.

It would be highly advantageous to provide implants for spinal surgeries such as interbody fusion, motion preservation and vertebral augmentation that may be inserted into the body in minimally invasive procedures.

SUMMARY OF THE INVENTION

Embodiments of the present invention disclose an implant comprising: (a) a base; and (b) a sequence of at least two segments including a first end segment and a second end segment, adjacent segments of the sequence being interconnected at a hinge, wherein the first end segment is interconnected with the base at a fixed hinge, and wherein the second end segment is interconnected with the base at a sliding interconnection, such that the base and the sequence of at least two segments assume an insertion state in which the sequence of segments is adjacent to the base, and a deployed state in which a part of the sequence of segments is deflected away from the base.

According to a further feature of certain embodiments of the present invention, in the deployed state, the base and the sequence of segments form a loop at least partially defining an enclosed volume.

According to a further feature of certain embodiments of the present invention, the sliding interconnection additionally allows pivotal movement of the second segment relative to the base.

According to a further feature of certain embodiments of the present invention, in the insertion state, the sliding interconnection is at a first position along the base, and wherein, in the deployed state, the sliding interconnection is displaced along the base from the first position towards the fixed hinge.

According to a further feature of certain embodiments of the present invention, the fixed hinge is located at one end of the base.

According to a further feature of certain embodiments of the present invention, the fixed hinge is located at a distal end of the base.

According to a further feature of certain embodiments of the present invention, the sliding interconnection includes an element slidingly engaged within a slot.

There is also provided according to the teachings of certain embodiments of the present invention, a method comprising the steps of: (a) providing the aforementioned implant; (b) introducing the implant in the insertion state into an intervertebral space; (c) deploying the implant to the deployed state; and (d) filling a space between the sequence of segments and the base with filler material to promote intervertebral fusion.

Additional features and advantages of the invention will become apparent from the following drawings and description.

BRIEF DESCRIPTION OF THE DRAWINGS

For a better understanding of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings:

FIG. 4d illustrates the implant in its fully deflected state in the spine with a tension element used to fix the maximal width, according to embodiments of the present invention;

FIGS. 6a(1-2) illustrate an implant with different number of segments in each side in a straightened and a fully deflected state, according to embodiments of the present invention;

FIGS. 6b(1-3) illustrate the implant deployment using a tension element, according to embodiments of the present invention;

FIGS. 6c(1-3) illustrate the implant deployment using an internal tensioning element, according to embodiments of the present invention;

FIGS. 7b(1-3) illustrate the elliptical implant in straightened, partially deflected and fully deflected states, according to embodiments of the present invention;

FIGS. 7c(1-2) illustrate the elliptical implant in straightened and fully deflected states with two internal tensioning elements, according to embodiments of the present invention;

FIGS. 9a(1-2) illustrate a 3D implant in straightened and fully deflected state, according to embodiments of the present invention;

FIGS. 9b(1-2) illustrate the 3D implant in straightened and fully deflected state in lateral views in between two vertebrae, according to embodiments of the present invention;

FIGS. 10a, 10c and 10d are schematic isometric views illustrating an implant according to a further embodiment of the present invention, the implant being shown in its straightened delivery state, an intermediate curved state and a fully open state, respectively; and FIG. 10b is a side view corresponding to the state of FIG. 10a.

DETAILED DESCRIPTION OF THE PREFERRED EMBODIMENTS

Figure 1:
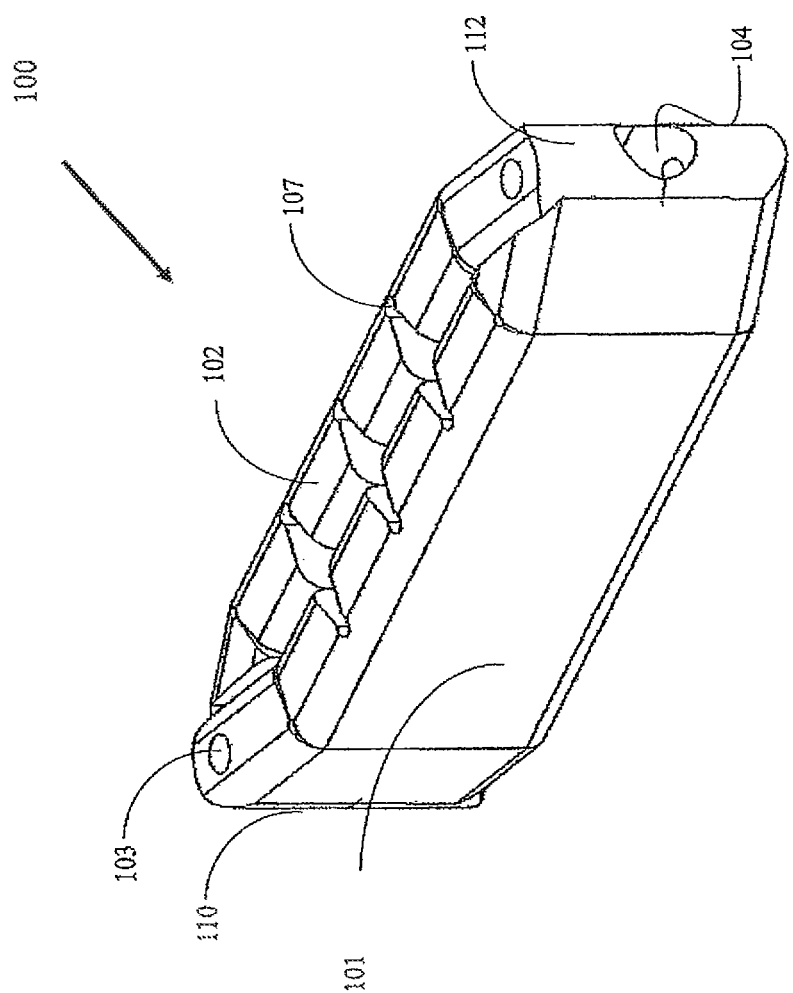
FIG. 1 illustrates an implant in a straightened state, according to embodiments of the present invention.

Certain embodiments of the present invention provide deflectable implants, systems and methods for implanting deflectable implants having a loop structure in a human or animal body. The loop structure is preferably pre-formed as a closed loop structure during delivery of the implant, but assumes a low-profile configuration folded on itself and/or straightened, to facilitate delivery via a minimally invasive procedure. In certain embodiments, the implant is arranged to open towards opposing sides of the axis defined by the direction of insertion, and may be symmetrical or asymmetrical about that axis, as will be exemplified below, thereby allowing the implant form and deployment sequence to be optimized for a range of different applications and approach directions.

In the context of the present description and claims, the word "loop" is used to refer to any structure in which following along the contiguous structure can lead back to the starting point while encircling at least one point lying outside the device. In certain cases, completion of the loop may be in the form of a sliding joint (as will be exemplified in FIG. 8 below). The word "loop" does not carry any implication of a circular or smooth shape, although such shapes are in certain cases preferred implementations of the loop structure when open.

The term "low profile" is used to refer to a configuration of a device in which at least one dimension of the device is significantly reduced, typically to less than 50% of the corresponding dimension of its deployed state, in order to facilitate delivery. In the present context, the low-profile configuration preferably has two transverse dimensions which are small compared to the direction of elongation, for easy delivery in a minimally invasive procedure, and the device opens up in one or two transverse dimensions when deployed.

Particularly preferred but non-limiting examples of implementations include intervertebral implants for supplementing, supporting or replacing an intervertebral disc as part of a fusion procedure or as a motion preserving implant, and intravertebral implants for supporting or restoring a vertebral body. The deflectable implants may include sequences of segments interconnected with effective hinges (such as conventional hinges or integral hinges) or may be formed with at least two elongated sides without clearly distinguished segments.

According to certain embodiments of the present invention, an implant that includes at least one sequence of segments, the sequence includes further at least two segments, more preferably at least three, and in many preferred cases four or more segments. The segments are interconnected at effective hinges, the sequence assuming a straightened or low curvature insertion state for insertion into the body, and being deflectable to a fully deflected state defined by abutment of abutment features of adjacent of the segments. Alternatively, the effective hinges may be configured to allow a range of angular motion beyond what is required to reach the fully open state. In the latter case, precise delineation of the desired final deployed state of the implant may be achieved by use of lateral tie elements, as will be described below. The implant preferably also includes a linkage, mechanically linked to at least part of at least one of the sequences of segments for deflecting the at least one sequence of segments from the insertion state towards the fully deflected state, wherein the at least one sequence is at least part of a loop structure assuming a low profile folded state with the at least one sequence in the insertion state, and wherein deflection of the at least one sequence towards the fully deflected state generates an open state of the loop structure.

According to certain embodiments of the present invention, a deflected implant may not have clearly distinct segments, but rather being formed from a single body of slotted or otherwise flexible material with at least first and second elongated sides interconnected at their proximal and distal ends, the at least first and second elongated interconnected sides assuming a straightened insertion state for insertion into a body, the at least first and second elongated interconnected sides being deflectable to a fully deflected loop inside the body, where the loop defines an enclosed volume with the upper and lower surfaces of the body. A linkage mechanically linked to at least part of at least one of the elongated interconnected sides, such as a tensioning element or a rod as two non limiting examples, may be used for deflecting the at least first and second elongated interconnected sides from the straightened insertion state towards the fully deflected loop inside the body.

According to certain embodiments of the present invention, an implant for interbody fusion is disclosed. The implant being deflectable to a fully deflected loop inside the body, where the loop defines an enclosed volume with the upper and lower surfaces of the bodies. The implant for interbody fusion further includes at least one opening in one or both of the elongated sides allowing access to the enclosed volume wherein the at least one opening is used to fill the enclosed volume in the fully deflected loop state with biocompatible filling materials for interbody fusion.

According to certain embodiments of the present invention, an implant for motion preservation is disclosed. The implant is deflectable to a fully deflected loop inside the body, where the loop defines an enclosed volume with the upper and lower surfaces of the body. The implant for interbody fusion further includes at least one opening in one or both of the elongated sides allowing access to the enclosed volume wherein the at least one opening is used to fill the enclosed volume in the fully deflected loop state with inert biocompatible filling materials applicable for motion preservation.

According to certain embodiments of the present invention, an implant system for implanting implants described herein above is disclosed. The implant system includes further an injector containing filling materials such as but not limited to biocompatible materials, bone grafts, bone chips, bone-growth enhancing agents for interbody fusion or inert filling materials, such as cement for interbody fusion or for stabilizing compression fractures, or other nucleus reinforcement or replacement material for motion preservation.

FIG. 1 illustrates an implant in a straightened state, according to embodiments of the present invention. Implant 100 includes at least one sequence of segments 102, with at least two segments, the segments being interconnected at effective hinges 107. Hinged interconnection is provided at one or both of the proximal and distal ends of the sequences of segments, allowing closing together of the two sequences of segments into low-profile closely adjacent positions when straightened, for convenient delivery in a minimally invasive operative procedure. The sequence of segments assumes a straightened or low curvature insertion state for insertion into the body as shown in FIG. 1. The two sequences of segments may be hingedly interconnected at both a distal end 110 and a proximal end 112 of each sequence. In other embodiments of the invention, the two sequences of segments are hingedly interconnected at one of a distal end 110 or a proximal end 112 of each sequence, preferably at the distal end 110, while completion of the loop at the other end is by some other form of interconnection, such as a sliding interconnection, as will be exemplified below with reference to FIG. 8.

A linkage (not shown in FIG. 1) is provided for deflecting the implant from the straightened insertion state towards the fully deflected state generating a loop structure in the body. In certain embodiments, the linkage is a tensioning element connected to the distal end 110 and threaded through an opening in the proximal end hinge 104. The tensioning element is used to reduce the distance between the distal and proximal ends of the implants' sequences.

An alternative set of non-limiting implementations of a linkage for deflecting the implant are arrangements for causing flexing of one or both segment sequences directly, such as an internal tensioning element as shown in FIG. 6B herein below. There may be a separate tensing element for each side (internal or external) or a single tensing element for both sides. In the case of two tensioning elements, each one may be activated separately or all may be activated simultaneously. The tensioning elements may be attached to the proximal end and to the distal end axels or to the individual segments or a combination. In certain embodiments of the present invention, the tensioning element may be a pull rod that is connected to the distal segments (in such a way that the pull rod does not interfere with the segment's movement) and extends through the proximal segments through an opening 104.

Actuation of a linkage for deflecting/opening the implant from its low-profile insertion state to its open deployed state is typically performed by operation of various actuating rod(s) or cable(s) or string(s) or strip(s) extending along the length of a minimally invasive delivery system, such as a conduit, all as is well known in the art. The motion or force required for actuation may originate from a manually operable handle, or from an automated or semi-automated mechanical or electrical actuator. Details of these arrangements a within the capabilities of a person having ordinary skill in the relevant art, and do not per se constitute part of the present invention. For conciseness, such details are therefore not described herein in detail.

The tensioning elements may be fabricated from metal (including steel, shape memory alloy, titanium or other) or polymer rods, metal or plastic cables or similar or a combination. The tensioning elements may be removed from the implant or remain completely or partially attached to the implant after deployment. The tensioning element may have a locking mechanism to enable controlled attachment and separation from the implant. The tensioning elements may have a mechanism to maintain a tensed configuration of the fully deflected implant.

Alternatively, the implant may be deflected by employing the properties of memory shape material or other materials with suitable resilient properties. Such memory shape or otherwise resilient material may constitute at least part of the implant's sequence of segments. In these embodiments, no linkage or tensing element may be necessary.

Figure 2:
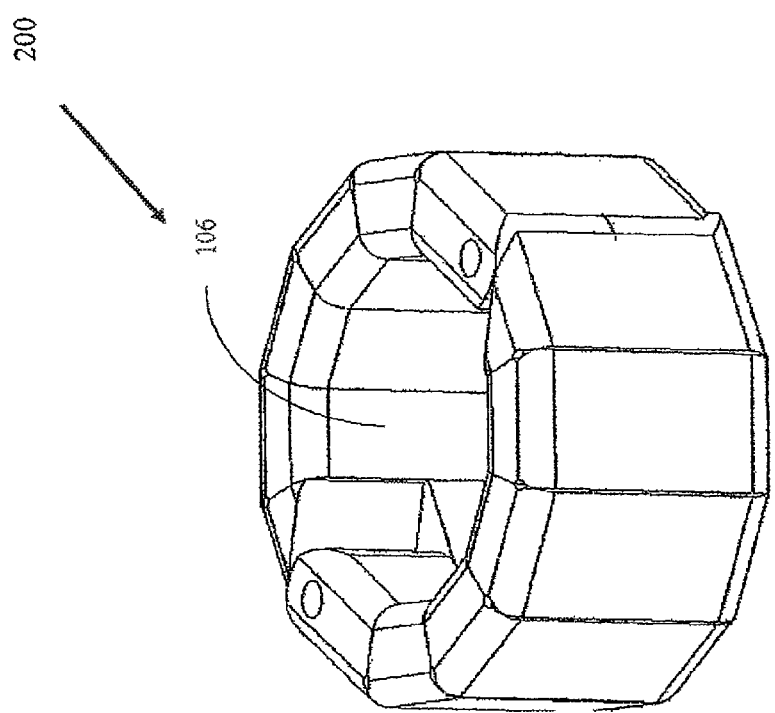
FIG. 2 illustrates the implant in a fully deflected state, according to embodiments of the present invention.

FIG. 2 illustrates the implant in a fully deflected state, according to embodiments of the present invention. When the tensing element is pulled relative to the proximal end, the implant is deflected to the fully deflected state 200 inside a body enclosing a volume 106 formed with the upper and the bottom surfaces of the body that may be for example the upper and lower endplates of vertebrae. Bone chips or bone enhancing agents or any other biological or other agent may be inserted into the enclosed volume 106. Optionally, there may be a window, a plurality of windows or similar opening in the fully deflected implant to facilitate insertion of filling materials into the enclosed volume 106.

Parenthetically, it should be noted that the term "enclosed volume" in the specification and claims refers to a volume which is encompassed on all sides in at least one plane, but does not necessarily imply closure above and below. In certain applications, the implants of the present invention are inserted between adjacent surfaces of tissue such that, together with the adjacent tissue surfaces, the enclosed volume becomes fully enclosed. Furthermore, the term "enclosed" does not rule out the presence of one or more opening through the enclosing structure, such as to allow filling of the enclosed volume through the wall of the implant, as will be discussed further herein.

According to certain embodiments of the present invention, the implant 100 may be deflected to its fully deflected state by linkage elements such as tensioning elements, inflation of balloons, by springs, by memory-shape material (such as Nitinol or similar materials), by turning a threaded rod, by a jacking mechanism, by injection of bone graft or other biologic material to promote fusion or by any other mechanical means. In other cases, the implant may be inherently resiliently biased to the deployed (open) state, and may temporarily be elastically deformed to the insertion state for deployment.

According to certain embodiments of the present invention, the implant 100 may be made of a polymer such as: Poly Ethylene, UHMWPE—Ultra High Molecular Weight Poly Ethylene, PEEK—Poly Ether Ether Ketone, Poly Ether Ketone Ketone, Poly Urethane as non limiting examples, or metal such as stainless steel, titanium, titanium alloy, shape memory alloy, as non limiting examples, or other material or a combination of such materials. The polymer materials may be reinforced with carbon fibers, glass fibers or similar filling materials known in the art.

According to certain embodiments of the present invention, the implant 100 may have a locking mechanism to retain the final fully deflected state. The locking mechanism may include a plurality of mechanisms that include cords, cables, strips, interconnections, snaps, or any other means known in the art, between each segment or a single mechanism for the entire implant or a combination. The locking mechanism may be fabricated from metal, including steel, shape memory alloy, titanium or other, or plastic or a combination. The locking mechanism may include a linkage or tensing element used to deflect the implant.

According to embodiments of the present invention, the implant may include a stabilizing arrangement to anchor the implant in the fully deflected state to the body. The locking arrangement may include a plurality of mechanisms that include cords, cables, strips, interconnections, snaps, ridges and any other means known in the art. The locking mechanism may be fabricated from metal, including steel, shape memory alloy, titanium or other, or plastic or a combination.

Figure 3A:
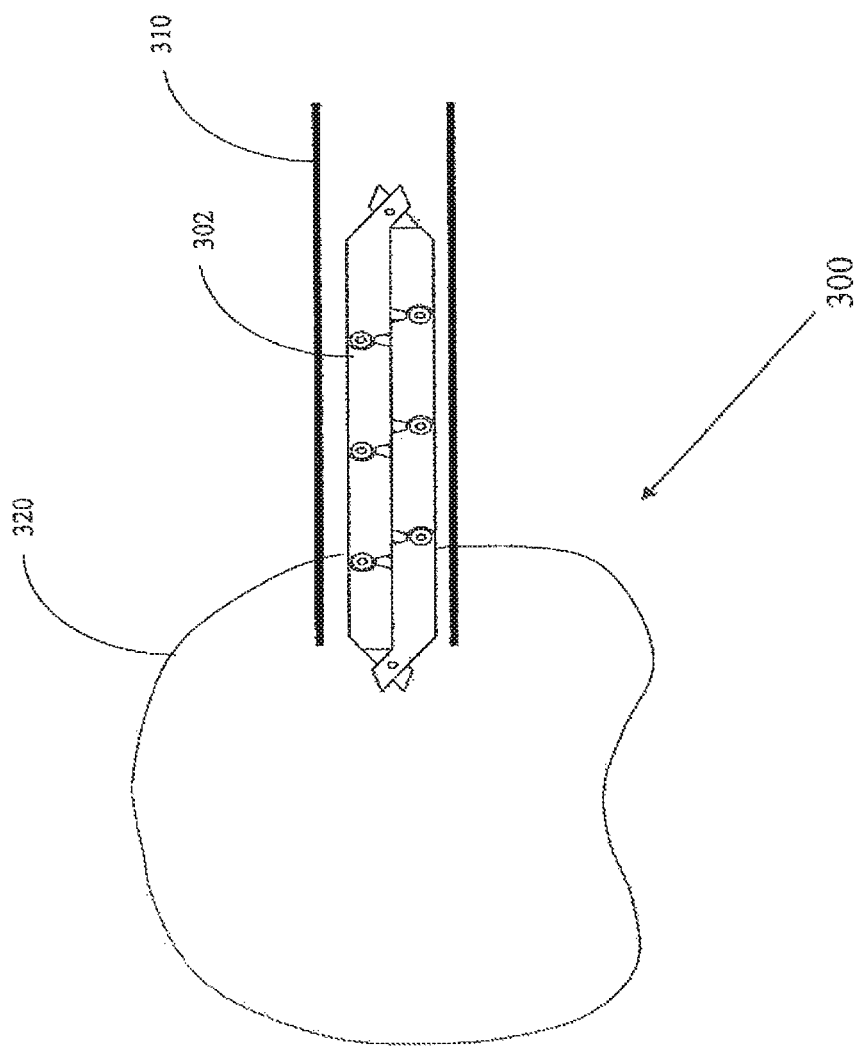
FIG. 3a illustrates an implant partially deployed, according to embodiments of the present invention.

FIG. 3a illustrates an implant partially deployed, according to embodiments of the present invention. The implant in a straightened state 302 is shown inside a conduit 310 ready for deployment in an evacuated disc space in a vertebra 320. The implant 302 may be inserted into the disc space 320 using a conduit 310 acting as a working channel. Alternatively, according to certain embodiments of the present invention, the implant may also be inserted into the disc space by being loaded on a tip of a guide and press-fit into the disc space. The implant 302 may have various heights and diameters to ideally accommodate the disc anatomy. In certain embodiments of the inventions, the implants may be designed as lordotic or kyphotic to accommodate the spine anatomy.

Figure 3B:
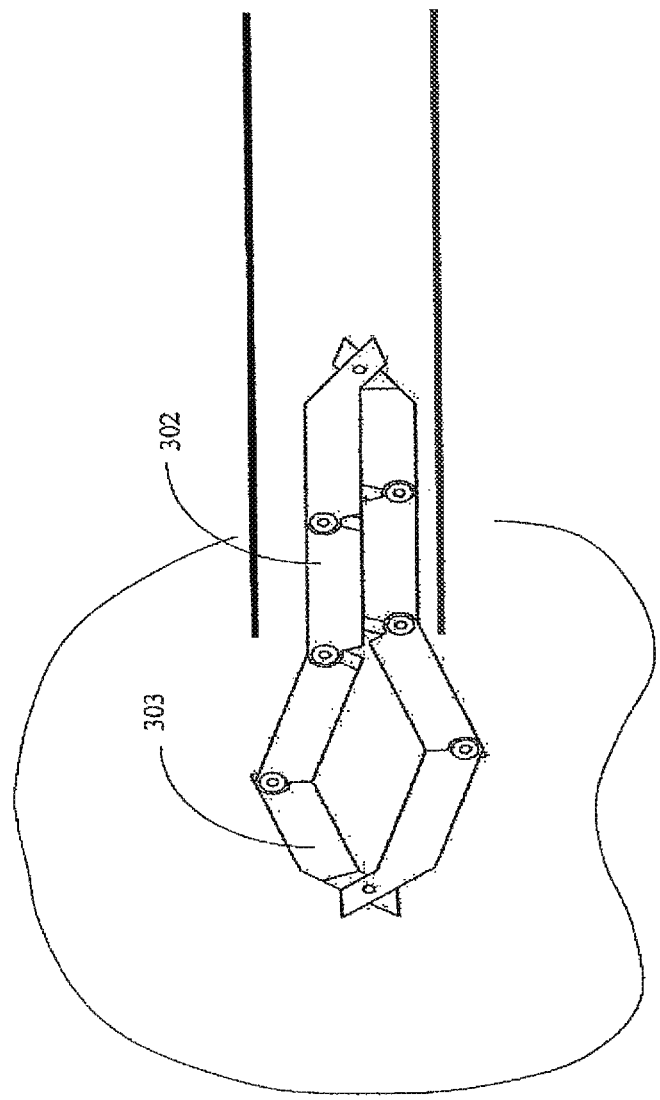
FIG. 3b illustrates the implant partially deflected in the spine, according to embodiments of the present invention.

FIG. 3b illustrates the implant partially deflected in a spine, according to embodiments of the present invention. A proximal part of the implant 302 is still in a straightened state inside a conduit 310 while a distal part is deployed and partially deflected in the evacuated disc space in a vertebra 320.

Figure 3C:
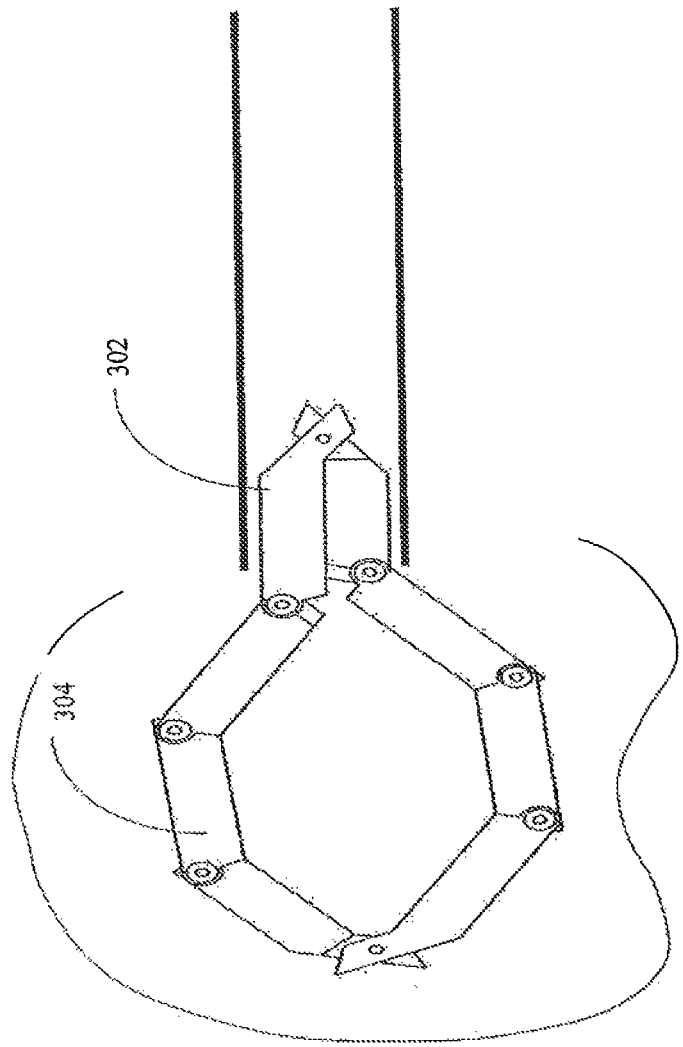
FIG. 3c illustrates the implant further deflected in the spine, according to embodiments of the present invention.

FIG. 3c illustrates the implant further deflected in the spine, according to embodiments of the present invention. A smaller part of the implant 302 with fewer segments is still in a straightened state inside a conduit 310 and a larger distal part 304 is deployed and deflected in the evacuated disc space in the vertebra 320.

Figure 3D:
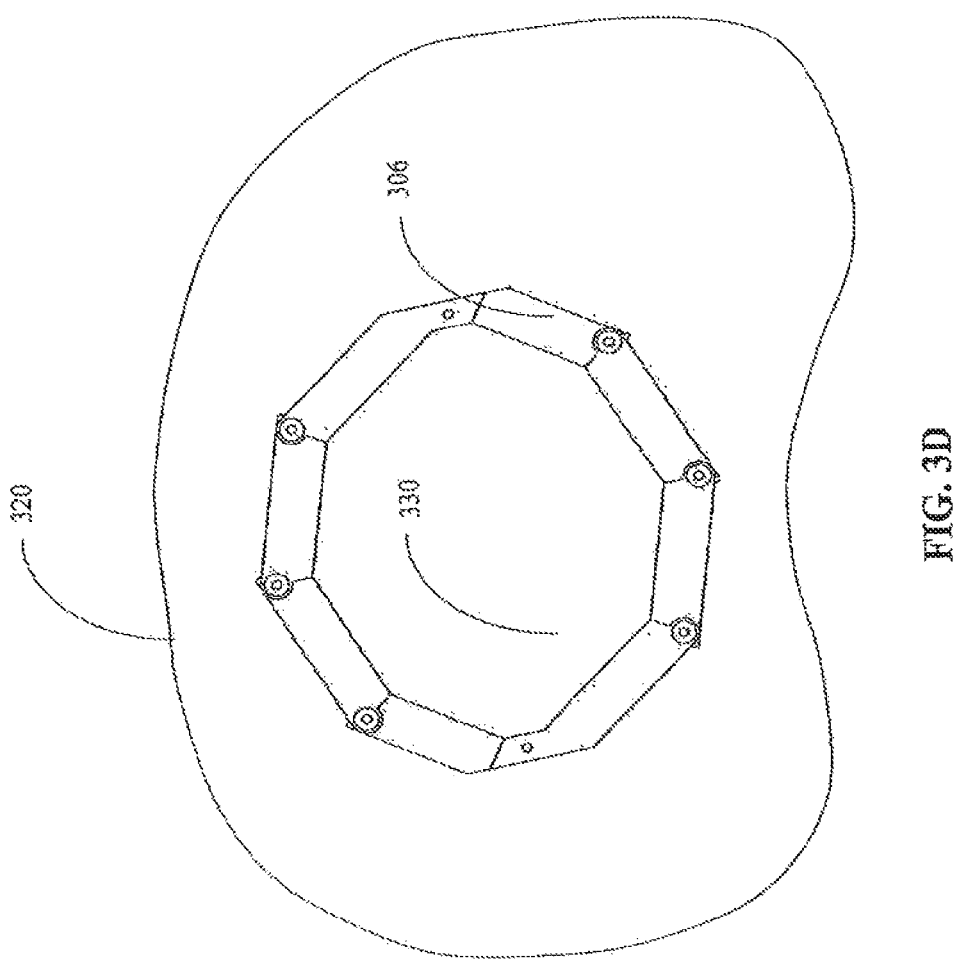
FIG. 3d illustrates the implant in its fully deflected state in the spine, according to embodiments of the present invention.

FIG. 3d illustrates the implant in its fully deflected state in the spine, according to embodiments of the present invention. Implant 308 is fully deflected in the spine 320. The implant in its fully deflected state encloses a volume 330 that may be filled with various filling materials for interbody fusion or other materials for motion preservation or for stabilizing a vertebra.

Figure 4A:
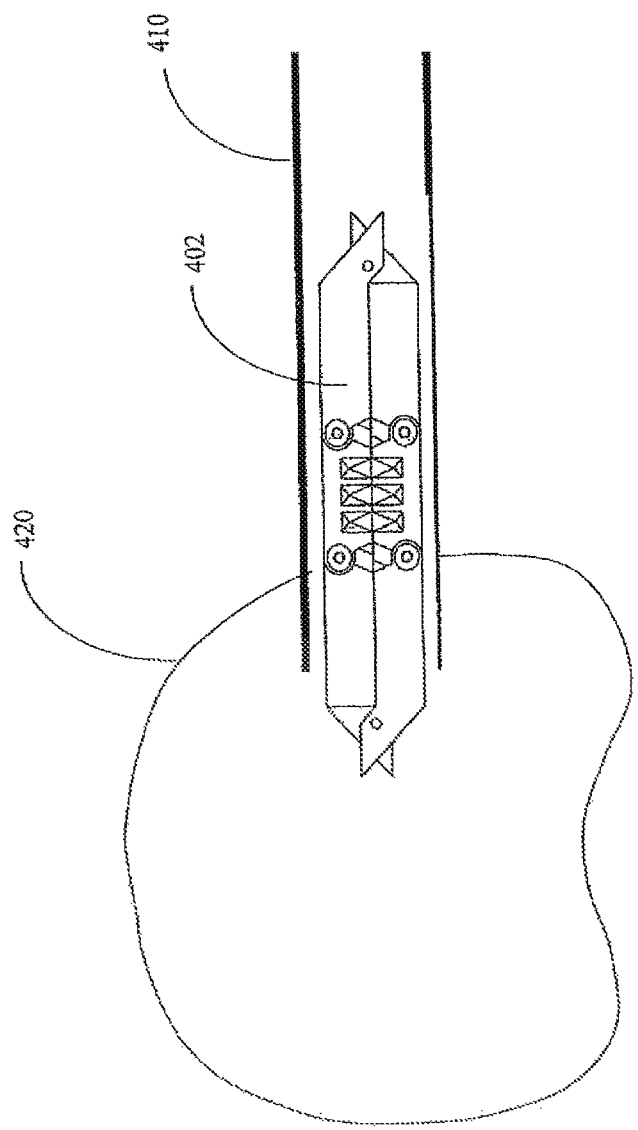
FIG. 4a-c illustrates an implant with fewer segments in straightened, partial and fully deflected states, according to embodiments of the present invention.
Figure 4B:
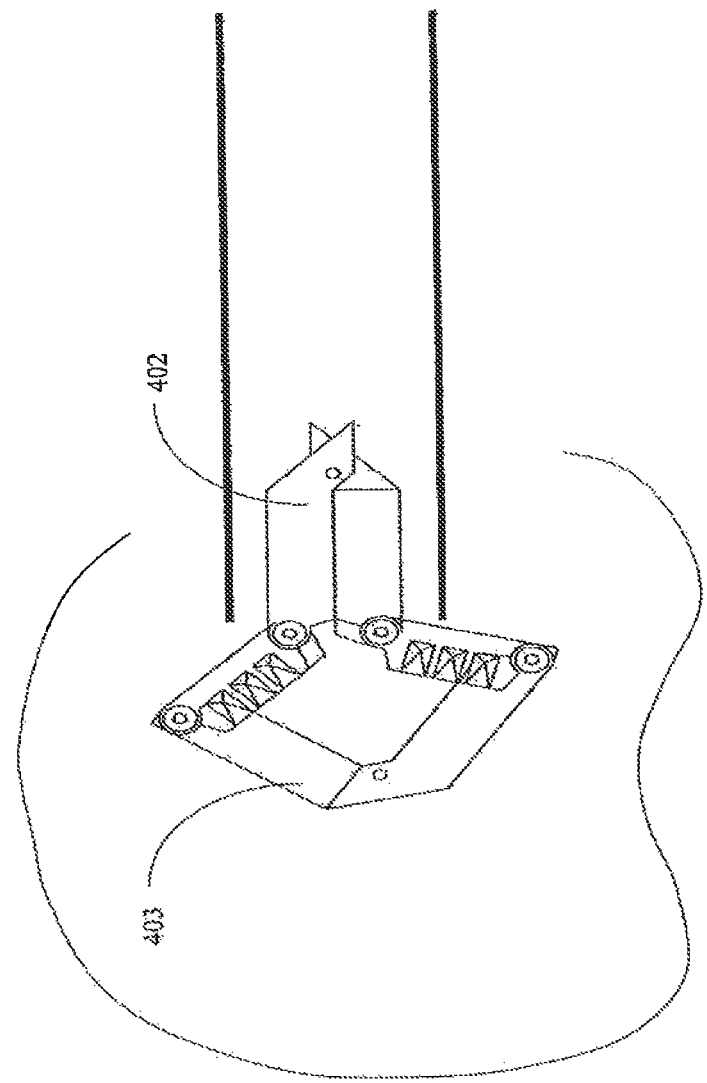
Figure 4C:
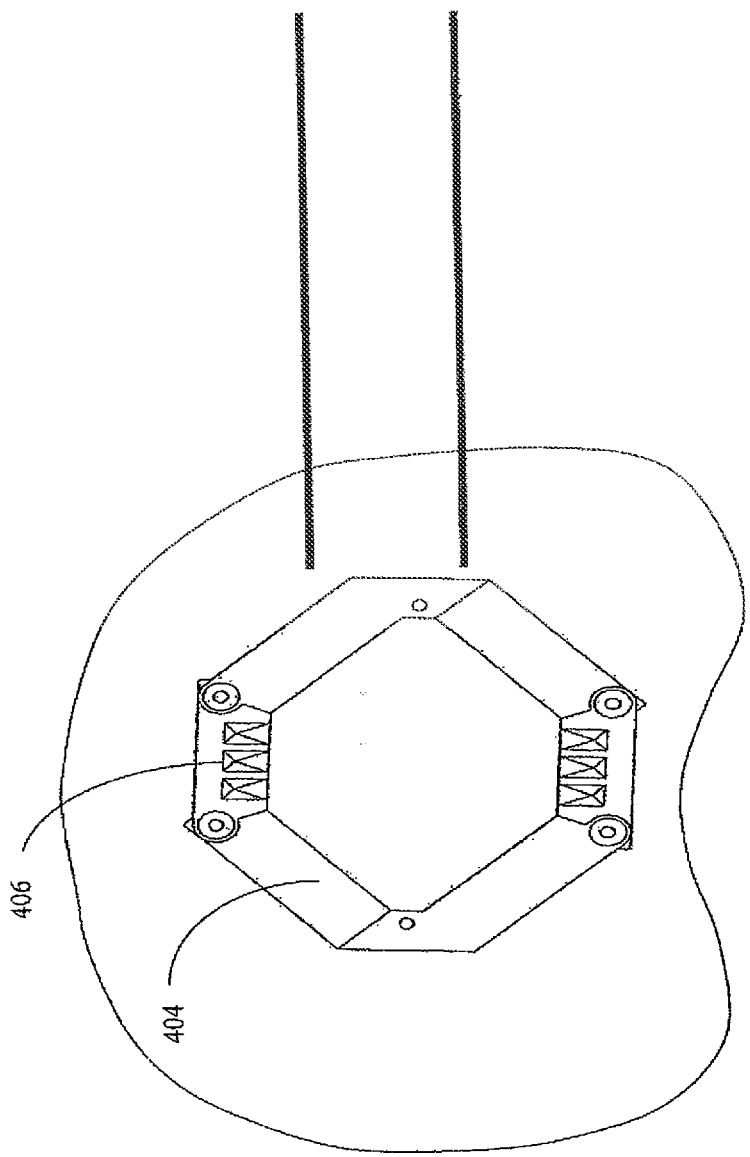

FIG. 4a-c illustrates an implant with fewer segments in straightened, partial and fully deflected states, according to embodiments of the present invention. FIG. 4a illustrates an implant with fewer segments in a straightened state 402 inside a conduit 410 ready for deployment in an evacuated disc space 420 in a spine. FIG. 4b illustrates the proximal part of the implant 402 still in a straightened state inside the conduit while the distal part 403 is deployed and partially deflected in the evacuated disc space in a vertebra. FIG. 4c illustrates the implant 404 fully deflected in the vertebra. In certain cases, implant 404 has projections 406 on the top and bottom surfaces. Projections 406 may be rigid or flexible and may fold flat onto the sides or into recesses. The projections 406 may be effective to scrape the upper and bottom vertebral endplates and/or help to anchor the implant in position relative to the adjacent tissue.

FIG. 4d illustrates the implant in its fully deflected state in the disc space with a transversely deployed tie element 410 used to fix the maximal width, according to embodiments of the present invention. Implant 404 is shown in its fully deflected state while tie element 410 is used to fix the maximal width of the implant inside the vertebra 420. The use of one or more lateral tie element serves to define the fully open state of the implant, typically as an alternative to using a limited range of motion of the hinges between segments to define the fully open configuration. This allows the implant to assume intermediate states during opening of the implant where the hinges between segments temporarily assume angles which are beyond the range of flexing allowed in the fully deployed state, such as is shown in FIG. 4B. In certain embodiments, a plurality of lateral tie elements may be provided spread along the length of the implant (not shown).

Figure 5A:
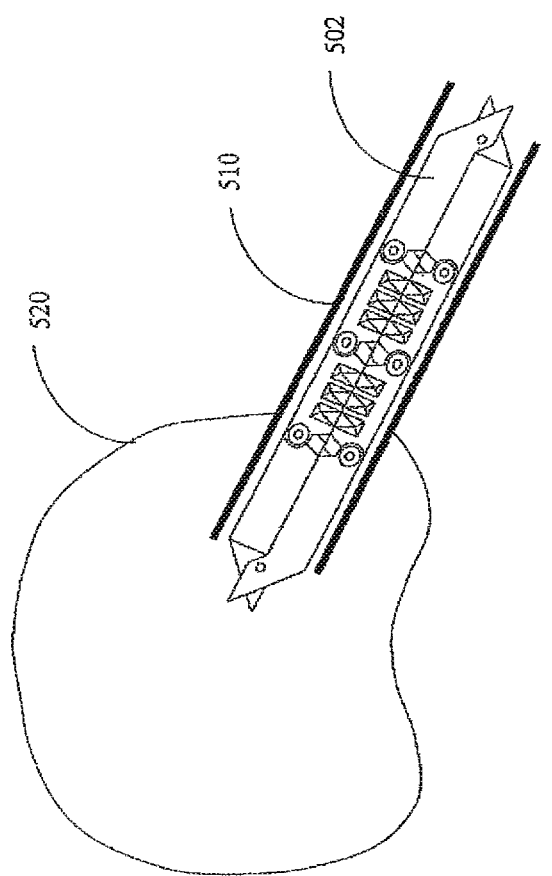
FIG. 5a-c illustrates an implant in straightened, partial and fully deflected states with final double ring shape, according to embodiments of the present invention.
Figure 5B:
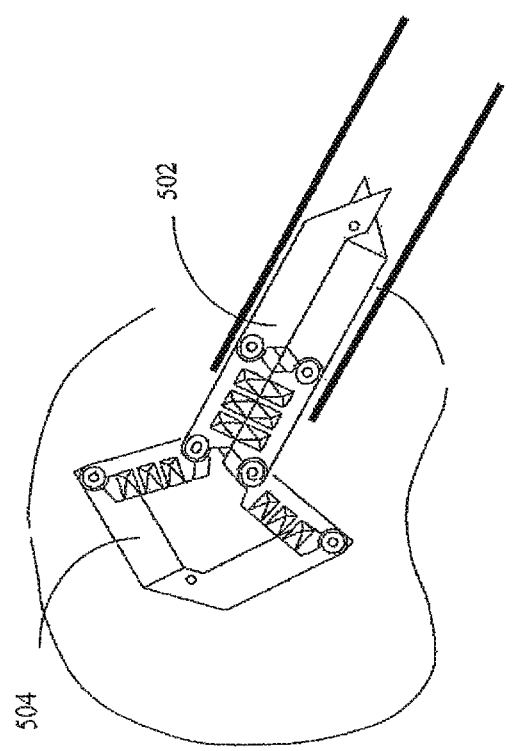
Figure 5C:
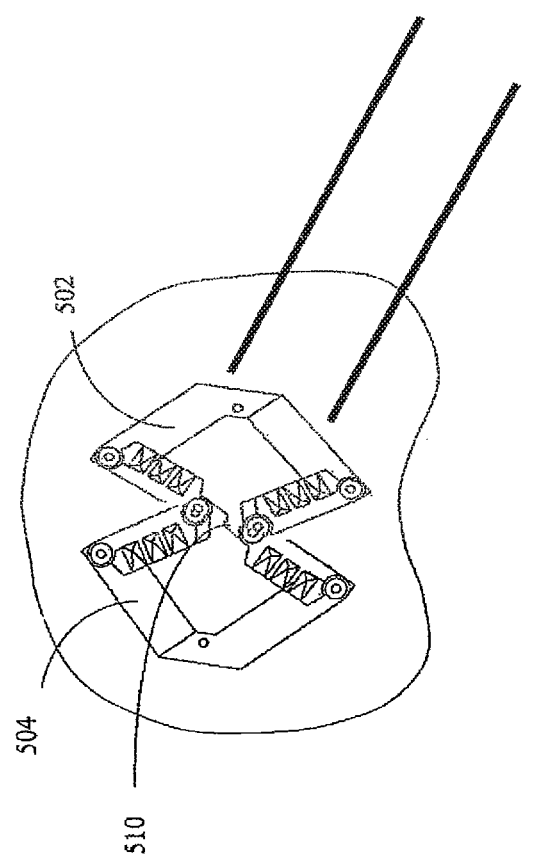

FIG. 5a-c illustrates an implant in straightened, partial and fully deflected states with final "double ring" or "figure-eight" shape, according to embodiments of the present invention. FIG. 5a illustrates a double ring implant in a straightened state 502 inside a conduit 510 ready for deployment in an evacuated disc space in a spine 520. FIG. 5b illustrates the proximal part of the implant 502 still in a straightened state inside the conduit while the distal part 504 is deployed and partially deflected in the evacuated disc space in the spine. FIG. 5c illustrates the implant fully deflected in the disc space with a double ring 502 and 504 shape. Tensioning element 510 is used to fix the medial part width of the implant as shown in the figure. It should be noted that the double loop or double ring is so called in view of the general overall form of the implant as illustrated, but that the narrow central region is not necessarily connected from side to side. Thus, this embodiment may also be viewed as an example of a loop insert which has a recess or concavity on at least one side, and which has a medial region which has a local minimum in a transverse dimension of the deployed implant.

FIGS. 6a(1-2) illustrate an implant with different number of segments in each side in a straightened and a fully deflected state, according to embodiments of the present invention. The asymmetric implant in a straightened state 602 is shown in FIG. 6a(1) in the left side and the fully deflected state 604 in FIG. 6a(2) in the right side. The asymmetric implant has 2 segments on the first side and 5 smaller segments on the second side. The sizes and the hinges of the asymmetric implant are designed such that in the fully deflected state 604 a smooth loop structure is obtained.

FIGS. 6b(1-3) illustrate the implant deployment using a tension element, according to embodiments of the present invention. FIG. 6b(1) illustrates the implant in its straitened state 602 in the right upper side with tensioning element 610. FIG. 6b(2) illustrates the implant in partially deflected state 604 with tensioning element 610 connected to the distal part 608 and is partially drawn back through the proximal part 609 such that the distance between the proximal 609 and the distal 608 ends is reduced. FIG. 6b(3) illustrates the implant in fully deflected state 606 in the left bottom side of the figure with tensioning element 610 connected to the distal part 608 and is drawn further back such that the distance between the proximal and the distal ends is further reduced in the fully deflected state. The tensioning elements may be removed from the implant or remain attached to the implant after deployment FIGS. 6c(1-3) illustrate the implant deployment using internal tensioning element, according to embodiments of the present invention. The asymmetric implant is shown in its straitened in FIG. 6c(1), partially deflected in FIG. 6c(2) and fully deflected states in FIG. 6c(3). The internal tensioning element threads the implant segments sequentially. The internal tensioning element is anchored to one side of the proximal part 614, threads through the distal part 616 and threads further through the second side of the proximal part 618. Pulling back tensioning element 620 reduces the distance between the ends of the distal and the proximal parts and deflects the implant to its fully deflected state as shown on the bottom left side of FIG. 6c. In other embodiments, at least two internal tensing elements may be used, each of them dedicated to each of at least two sequences of segments.

Figure 7A:
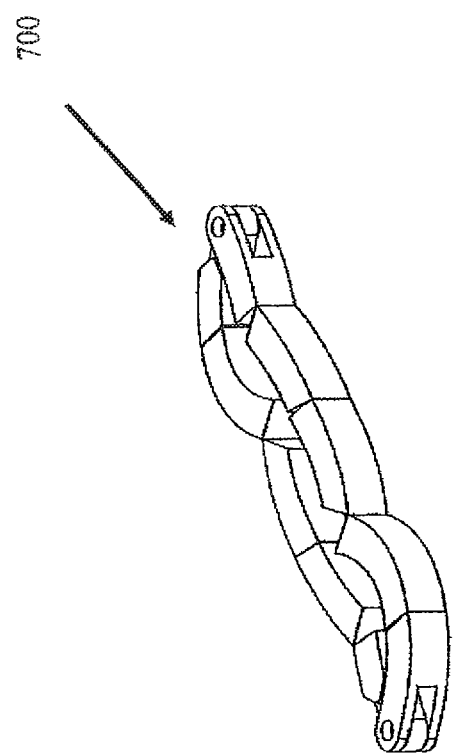
FIG. 7a illustrates an elliptical shape implant in a straightened state, according to embodiments of the present invention.

FIG. 7a illustrates an elliptical shape implant in a straightened state, according to embodiments of the present invention. Implant 700 is shown in its straightened state and is another asymmetric implant according to embodiments of the present invention where the two sequences of segments between the proximal and distal ends are not a minor reflection of each other.

FIGS. 7b(1-3) illustrate the elliptical implant in straightened, partially deflected and fully deflected states, according to embodiments of the present invention. FIG. 7b(1) illustrates the elliptical implant straightened state 702 inside the conduit, FIG. 7b(2) illustrates the partially deflected state 704 when partially deployed and FIG. 7b(3) illustrates the fully deflected state 706 when fully deployed. The elliptical implant as shown here deploys as an off-axis ellipse, i.e., where neither the major nor the minor axis of the ellipse is aligned with the axis defined by the deployment direction. The ability to deploy an asymmetric implant, or a symmetric implant with an orientation offset relative to the deployment direction, is particularly valuable for allowing appropriate deployment of inserts during procedures with a range of different access directions.

FIGS. 7c(1-2) illustrates the elliptical implant in straightened FIG. 7c(1) and fully deflected FIG. 7c(2) states with two internal tensioning elements, according to embodiments of the present invention. Two internal tensioning elements 718 and 719 are anchored to two sides of the distal end segments 708 and 709. The two tensioning elements are threaded through the segments sequences from each side of the implant. The two tensioning elements may extend along one or along both sides of the elongated sequences of segments to allow selective deflection of the implant towards the implant fully deflected state. The two tensioning elements may be pulled simultaneously or one after the other deflecting the implant to the fully elliptical deflected state shown on the bottom left in FIG. 7c(2).

Figure 8:
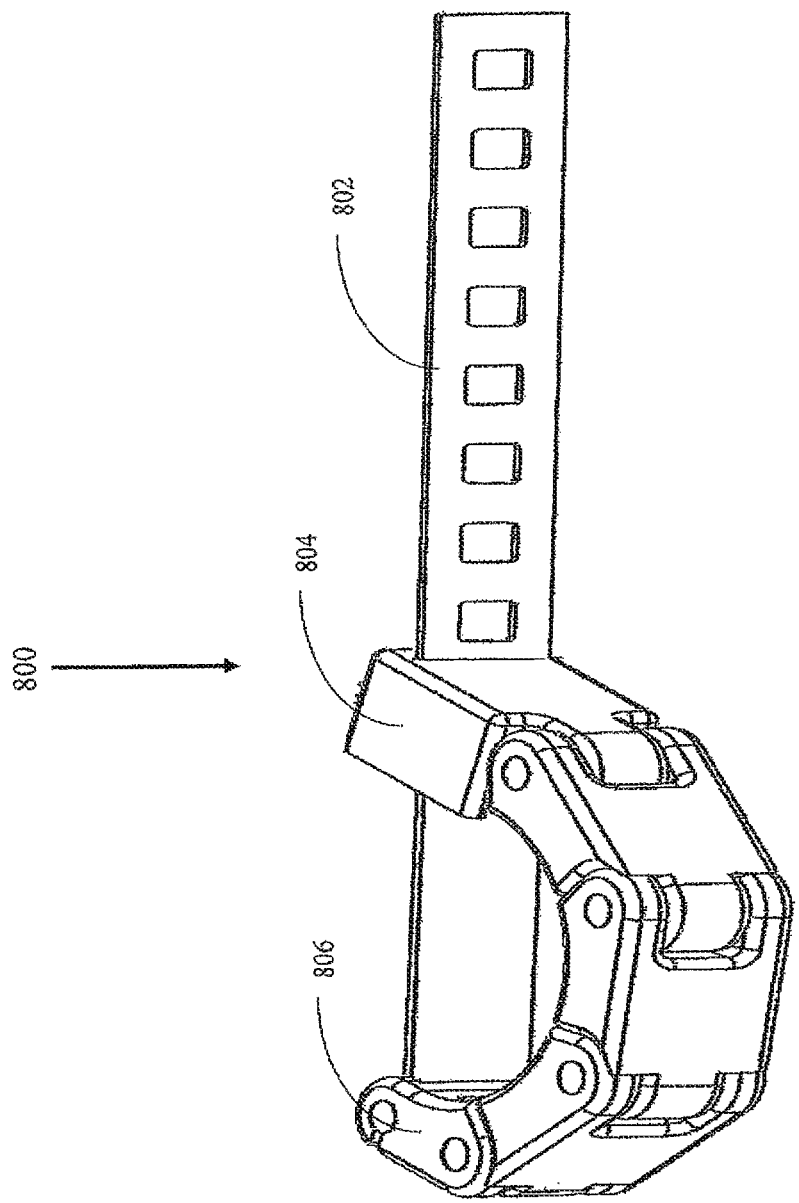
FIG. 8 illustrates a D-shape implant in fully deflected states, according to embodiments of the present invention.

FIG. 8 illustrates a D shape implant 800 in a fully deflected state, according to embodiments of the present invention. The D-shape implant is another asymmetric implant according to embodiments of the present invention. The D-shape implant has one flat segment (a "base") 802 on first side and a sequence of segments interconnected with hinges on the second side. The sequence of segments includes a first end segment 806 interconnected with base 802 at a fixed hinge, and a second end segment 804 interconnected with base 802 at a sliding interconnection. Hinge axes of the hinges interconnecting the sequence of segments and of the fixed hinge connecting first end segment 806 with base 802 are all parallel. The D-shape implant has a straightened insertion state with low cross section and a fully deflected state as shown in FIG. 8 in which the base and the sequence of segments define an outer perimeter of a single-loop implant. Deployment of the sequence of segments from the insertion state to the deployed state corresponds to expansion of the implant asymmetrically to one side of the base. In certain embodiments, the sequence of segments is deflected by applying longitudinal pressure to the proximal part of the sequence, thus causing a relative movement between the sequence's segments and the flat segment without the need for any linkage or tensing element.

FIGS. 9a(1-2) illustrate a three dimensional (3D) implant in straightened and fully deflected states, according to embodiments of the present invention. FIG. 9a(1) shows the 3D implant in its straightened insertion state 940 and FIG. 9a(2) shows the 3D implant in its fully deflected state 950. The 3D implant may be opened horizontally 905, in the body axial plane or vertically 906 in the body sagittal plane or at any other angle. Furthermore, the 3D implant may be opened in more than one plane simultaneously or sequentially. In the 3D case the implant has more than two sides (901, 902, 903 and 904 for example) forming a three dimensional shape.

FIGS. 9b(1-2) illustrate the 3D implant in straightened and fully deflected state in lateral views in between two vertebrae, according to embodiments of the present invention. FIG. 9b(1) shows the upper vertebra 910 bottom vertebra 912 and the 3D implant 914 positioned in between the two vertebrae in its straightened insertion state 940. FIG. 9b(2) shows the upper vertebra 910 bottom vertebra 912 and the 3D implant 916 positioned in between the two vertebrae in its fully deflected state 950. The deflected implant 916 increases the height between the two vertebrae in the sagittal plane and can be used to fix compression fracture of discs by restoring the height between the two vertebrae thus the deflected implant 916 may be used for vertebral augmentation. The 3D implant illustrated in FIGS. 9a-b is merely a non limiting example of a 3D implant according to embodiments of the present invention. Other geometries with larger contact surfaces with the two vertebrae for example may be designed and are in the scope of the present invention.

Another application of a 3D implant is for vertebral augmentation with or without the addition of a stabilizing agent such as cement for treating degenerative or trauma vertebra fracture cases.

According to embodiments of the present invention, the fully deflected state of the implants may be toroidal polyhedrons, ring toroids, elliptical toroids and multi-ring toroids as shown in the various drawings which are merely non limiting examples of deflected implants that are in the scope of the present invention and where other deflected implants may be designed by persons skilled in the art according to embodiments of the present invention.

Turning finally to FIGS. 10a-10d, it should be noted that, where hinged interconnection is used between the elongated elements, the hinge axis need not be perpendicular to the length of the implant. By way of one non-limiting example, FIGS. 10a-10d illustrate an example of an implant 1000 in which a hinge axis 1002a and 1002b for folding of the implant extends along a diameter or length of the deployed implant.

In this case, in the straightened state of FIGS. 10a and 10b, hinge axes 1002a and 1002b are not aligned, and the implant is locked against opening. Only when the implant is deflected to the state of FIG. 10c do the two hinge axes come into alignment, allowing the pivotal opening of the two halves of the implant to assume the open configuration of FIG. 10d. Here too, all the options of various actuating linkages or use of inherent resilient biasing are applicable.

In summary, deflectable implants described above may be used for interbody fusion, for motion preservation and for vertebral augmentation. The deflectable implants may be used as intervertebral implants or/and intravertebral implants. Other spinal and non-spinal applications of such implants are also envisaged.

Advantageously, embodiments of the deflectable implants described above have low cross section in their straightened insertion state allowing them to be inserted through a small orifice in the skin.

Another advantage of certain embodiments of the deflectable implants described above is that their fully deflected state may fill the intervertebral disc space replacing a sick disc tissue.

Another advantage of certain embodiments of the deflectable implants described above is that their fully deflected state may have at least one opening that may be filled with bone grafts and other biocompatible materials for interbody fusion.

Another advantage of certain embodiments of the deflectable implants described above is that their fully deflected state may have at least one opening that may be filled with inert materials for motion preservation.

Another advantage of certain embodiments of the deflectable implants described above is that their fully deflected state in more than one plane and particularly in the sagittal plane may be used for vertebral augmentation.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description.

What is claimed is:

1. A single-loop implant comprising:
   (a) a base; and
   (b) a sequence of at least two segments including a first end segment and a second end segment, adjacent segments of said sequence being interconnected at a hinge which defines a hinge axis about which said adjacent segments pivot,
   wherein said first end segment is interconnected with said base at a fixed hinge, said fixed hinge defining a hinge axis about which said first end segment pivots relative to said base, and wherein said second end segment is interconnected with said base at a sliding interconnection,
   such that said base and said sequence of at least two segments assume an insertion state in which said sequence of segments is adjacent to said base, and a deployed state in which a part of said sequence of segments is deflected away from said base, wherein said base and said sequence of segments in said deployed state define an outer perimeter of the single-loop implant,
   wherein all of said hinge axes are parallel,
   and wherein, in said insertion state, said sliding interconnection is at a first position along said base, and wherein, in said deployed state, said sliding interconnection is displaced over a flat surface of said base from said first position towards said fixed hinge.

2. The implant of claim 1, wherein, in said deployed state, said base and said sequence of segments form a loop at least partially defining an enclosed volume.

3. The implant of claim 1, wherein said sliding interconnection additionally allows pivotal movement of said second segment relative to said base.

4. The implant of claim 1, wherein said fixed hinge is located at one end of said base.

5. The implant of claim 4, wherein said fixed hinge is located at a distal end of said base.

6. The implant of claim 1, wherein said sliding interconnection includes an element slidingly engaged within a slot.

7. A method comprising the steps of:
   (a) providing the implant of claim 1;
   (b) introducing said implant in said insertion state into an intervertebral space;
   (c) deploying said implant to said deployed state; and
   (d) filling a space between said sequence of segments and said base with filler material to promote intervertebral fusion.

8. An implant comprising:
   (a) a base; and
   (b) a sequence of at least two segments including a first end segment and a second end segment, adjacent segments of said sequence being interconnected at a hinge which defines a hinge axis about which said adjacent segments pivot,
   wherein said first end segment is interconnected with said base at a fixed hinge, said fixed hinge defining a hinge axis about which said first end segment pivots relative to said base. and wherein said second end segment is interconnected with said base at a sliding interconnection,
   such that said base and said sequence of at least two segments assume an insertion state in which said sequence of segments is adjacent to said base, and a deployed state in which a part of said sequence of segments is deflected away from said base,
   wherein deployment of said sequence of at least two segments from said insertion state to said deployed state corresponds to expansion of the implant asymmetrically to one side of said base,
   wherein all of said hinge axes are parallel, and wherein, in said insertion state, said sliding interconnection is at a first position along said base, and wherein, in said deployed state, said sliding interconnection is displaced over a flat surface of said base from said first position towards said fixed hinge.

9. The implant of claim 8, wherein, in said deployed state, said base and said sequence of segments form a loop at least partially defining an enclosed volume.

10. The implant of claim 8. wherein said sliding interconnection additional allows pivotal movement of said second end segment relative to said base.

11. The implant of claim 8, wherein said fixed hinge is located at one end of said base.

12. The implant of claim 11, wherein said fixed hinge is located at a distal end of said base.

13. The implant of claim 8. wherein said sliding interconnection includes an element slidingly engaged within a slot.

14. A method comprising the steps of:
   (a) providing the implant of claim 8;
   (b) introducing said implant in said insertion state into an intervertebral space;
   (c) deploying said implant to said deployed state; and
   (d) filling a space between said sequence of segments and said base with filler material to promote intervertebral fusion.

* * * * *